United States Patent [19]

Lademann et al.

[11] 4,056,455
[45] Nov. 1, 1977

[54] PROCESS FOR THE CONTINUOUS PREPARATION OF MONO- OR DI-(TRICHLOROMETHYL)-BENZENES

[75] Inventors: Rudolf Lademann, Kelheim, Taunus; Franz Landauer, Frankfurt am Main; Heinrich Lenzmann, Kelheim, Taunus; Klaus Schmiedel, Konigstein, Taunus; Wolfram Schwiersch, Frankfurt am Main, all of Germany

[73] Assignee: Hoechst Aktiengesellschaft, Frankfurt am Main, Germany

[21] Appl. No.: 701,819

[22] Filed: July 1, 1976

[30] Foreign Application Priority Data

July 5, 1975 Germany .............................. 2530094

[51] Int. Cl.$^2$ ............................................. B01J 1/10
[52] U.S. Cl. ............................................. 204/163 R
[58] Field of Search ...................... 204/163 R, 163 HE

[56] References Cited

U.S. PATENT DOCUMENTS

| 2,132,361 | 10/1938 | Osswald et al. | 204/163 R |
| 2,695,873 | 11/1954 | Loverde | 204/163 R |
| 2,817,632 | 12/1957 | Mayor | 204/163 R |
| 2,998,459 | 8/1961 | Baker et al. | 204/163 R X |
| 3,442,960 | 5/1969 | DePuy et al. | 204/163 R X |

*Primary Examiner*—Leland A. Sebastian
*Attorney, Agent, or Firm*—Curtis, Morris & Safford

[57] ABSTRACT

Continuous preparation of mono- or di-(trichloromethyl)-benzenes or of mono- or di-(trichloromethyl)-benzenes substituted in the benzene ring by halogen atoms from the corresponding mono- or dimethylbenzenes and chlorine in several steps with radiation by means of rays of high energy, is effected by reacting mono- or dimethylbenzene with chlorine in 4 to 14 steps, at a temperature in the range of from 20° to 130° C, whereby chlorine is introduced into the second step and the following steps, the resulting waste gas is introduced into step 1 and chlorine contained in the waste gas is reacted in reactor 1 with fresh mono- and dimethylbenzene. A preferred embodiment for carrying out the process is reaction in a reactor arrangement in cascade form, wherein the number of steps corresponds to the number of reactors and wherein as reactors circulation reactors are used.

9 Claims, 3 Drawing Figures

PROCESS FOR THE CONTINUOUS PREPARATION OF MONO- OR DI-(TRICHLOROMETHYL)-BENZENES

Several processes have already been proposed for the industrial chlorination of toluene yielding benzotrichloride, partially carried out discontinuously, partially continuously. These processes however present various disadvantages. Towards the end of the reaction, when the content of hydrogen atoms in the side chain position capable of being substituted is relatively low, secondary reactions, for example a chlorination in the nucleus frequently take place owing to the excessive amount of chlorine, especially in the case when there is no longer a sufficient quantity of free radical forming agents in this last phase or when only thermally initiated radical chains may be formed in the case of an insufficient radiation or no radiation at all. Trials have been made to minimize the disadvantages of said processes by diluting the chlorine used in an excess with an inert gas for example nitrogen, in order to avoid undesired secondary reactions. This proceeding however has the disadvantage that a high quantity of chlorine passes into the waste gas with the inert gas, which necessitates an uneconomic high-pollution chlorine annihilation plant or that a separate second chlorination plant must be operated as described in German Auslegeschrift No. 2,152,608. Coupling several plants however has always the great disadvantage in practice that a failure of one plant, either for technical or economic reasons, also requires a stopping of the other plants. The process of German Auslegeschrift No. 2,152,608 moreover has the disadvantage that not only the secondary reaction is hindered, but also the desired main reaction, by the dilution of chlorine with inert gas. When representing the results obtained in Table 3 of German Auslegeschrift No. 2,152,608 in such a way that the reduction of the benzalchloride content (in % by weight) is compared with the increase of the content of products chlorinated in the nucleus or of highly chlorinated products (in % by weight) it can be seen that the addition of inert gas in the course of the chlorination is of no advantage with regard to the repression of the secondary reaction up to a benzalchloride content of considerably less than 2%.

Concerning the side chain chlorination of alkylaromatic compounds, especially the complete chlorination of methyl groups in the benzene ring, there must be mentioned three competing reactions:

a. the desired perchlorination of the methyl groups,
b. substitutions in the aromatic ring and
c. an addition of chlorine to the benzene ring.

The secondary reaction in the reaction system mentioned under (c) has been practically ignored hitherto in the technical literature. All three reactions are influenced by different factors. Only an exact consideration of these factors allows carrying out the reaction in optimum manner and constructing the apparatus required for this purpose.

Table 1 shows the result obtained in six chlorination tests, wherein toluene and chlorine had been reacted discontinuously to yield benzotrichloride under different, but comparable conditions.

TABLE 1

Discontinuous chlorinations of toluene yielding benzotrichloride

| test No. | feeding toluene mol | feeding chlorine mol/h | test duration h | test temperature ° C | engineering material of the reactor | source of light | final content of secondary products in benzotrichloride | |
|---|---|---|---|---|---|---|---|---|
| | | | | | | | benzalchloride % by weight | o-, m-, p-chloro compounds % by weight |
| 1 | 10 | 1.43 | 26 | 105 | glass | Hg-vapor lamp | 0.23 | 0.5 |
| 2 | 10 | 1.43 | 26 | 100–170 | glass | Hg-vapor lamp | <0.05 | 2.0 |
| 3 | 10 | 1.43 | 23 | 85 | glass | Hg-vapor lamp | 0.16 | 0.06 |
| 4 | 10 | 1.43 | 26 | 105 | nickel | Hg-vapor lamp | 1.5 | 2.5 |
| 5 | 10 | 1.43 | 26 | 105 | nickel | none | 48.8 | 7.1 |
| 6 | 10 | 1.43 | 26.5 | 95 | glass | daylight fluorescent lamp | 2.1 | 0.5 |

It is generally known that the side chain chlorination of alkylaromatic compounds is catalyzed by ultraviolet light and that on the other hand a thermal catalysis of this reaction is also possible. The latter however has disadvantages which will be treated hereafter.

It has now been found that the reaction liquid in the course of the chlorination with radiation, for example with ultraviolet light, remains transparent for the eye at any time, but becomes impermeable to a high extent for the catalytically active radiation after a relatively short period owing to the fact that the effective radiation is practically completely absorbed by the reaction medium within a penetration depth of a few millimeters. This signifies for a chlorination plant comprising vessels connected in cascade form that the reaction is practically no longer sufficiently catalyzed by ultraviolet light in the reactors connected after the reactor for the initial chlorination so that it must be initiated additionally thermally in said reactors, which process requires temperatures of from 150° to 200° C, as it may be seen in the prior art processes. This has however several disadvantages, for example a high energy consumption as well as an increase in the formation of by-products, for example products chlorinated in the nucleus (cf. Table 1, test 2). It has moreover been noticed that it may be especially advantageous to initiate the reaction by ultraviolet light just in the stage following the initial chlorination (cf. Table 1, tests 5 and 4). On the other hand it has been found that a sufficient catalytical effect may be attained in the initial chlorination, i.e., the formation of benzyl chlorides from methyl benzenes, by radiation, for example with an ordinary daylight fluorescent lamp (cf. Table 1, test 6).

With regard to the reaction temperatures in the side chain chlorination it is known that a reaction of chlorine with toluene takes place when subjecting to radiation at a temperature of up to −80° C (cf. G. Book and J. Eggert, Z. Elektrochem. u. Angew. Chem. 29 (1923), pages 521 – 527). Reaction conditions of this kind are however of no interest for industrial processes as the considerable quantity of heat liberated in said process may only be dissipated from the chlorination in complicated and expensive manner.

It is finally known that the chlorination may also be performed at higher temperatures, for example of from 150° to 200° C. The formation of by-products chlorinated in the nucleus however increases at such high temperatures (cf. Table 1, test 2). The chlorination in the nucleus at low temperatures only takes place in a sufficiently rapid manner in the presence of catalysts, for example iron halides, whereas the reaction speed is sufficiently rapid at higher temperatures in the absence of catalysts, so that the reaction course of the chlorination in the nucleus may be well followed. Chlorinations in the nucleus due to iron catalysis however could not be avoided even in the known industrial processes, as said processes are carried out in enamel or nickel apparatuses, which apparatuses cannot be garantueed to be completely free from iron (cf. Table 1, tests 1 and 4). The content or iron of pure nickel may amount up to 0.2% by weight. The apparatuses for the side chlorination in large-scale processes comprise great vessels provided with submergible ultraviolet ray lamps. These ultraviolet ray lamps are inefficient for a great part of the reaction volume owing to the fact that the permeability of the reaction medium for ultraviolet light decreases at rather high chlorination degrees, as already mentioned. A consequence of the low initiation of the side chain chlorination by the unutilizable ultraviolet lamps is an increase of the undesired chlorination in the nucleus (cf. Table 1, tests 6, 4 and 1), owing to the fact that the added quantity of chlorine cannot be reacted rapidly enough in the desired manner and that a high chlorine content favors secondary reactions. All these disadvantages caused by traces of iron from the reactor engineering material may be avoided by using glass as construction material (cf. Table 1, tests 1, 3 and 6).

Besides the chlorination in the nucleus a further secondary reaction may occur, as indicated sub (c), namely the addition of chlorine, for example to yield chlorocyclohexane derivatives, favored by a chlorine concentration which is too high and by radiation. For suppressing said reaction the chlorine concentration must be adapted to the reaction speed of the side chain chlorination.

Examinations of the main reaction, i.e., the side chain chlorination, by using p-chlorotoluene have shown that the reaction speeds $K_1$ of the three consecutive chlorination steps are as follows:

reaction:
p-chlorotoluene → p-chlorobenzylchloride = $K_1$
p-chlorobenzylchloride → p-chlorobenzalchloride = $K_2$
p-chlorobenzalchloride → p-chlorobenzotrichloride = $K_3$ $$\frac{K_1}{K_2} = 7 \text{ to } 8; \qquad \frac{K_2}{K_3} = 6 \text{ to } 7.$$

This signifies that p-chlorotoluene is reacted 42 to 56 times faster to yield p-chlorobenzylchloride than p-chlorobenzalchloride to yield p-chlorobenzotrichloride with the same chlorine concentration, provided that the concentrations of the aromatic reactants are the same. When taking further into account that the reaction speed depends linearly on the concentration of the organic reactants, it may be deduced from the aforesaid facts that the main reaction must be considerably slower at its end, for example when only 0.3% by mole of benzalchloride are present in the reaction mixture besides benzotrichloride than at the beginning when there is still a concentration of methyl benzene compound of practically 100% by mole. Although this considerable diminution of the reactivity in the course of the reaction may be partially compensated by the increase of the chlorine concentration, from the beginning to the end of the reaction by about 100% the fact is still evident that the reaction begins rapidly, but terminates slowly and that the chlorine concentration in the waste gas increases towards the end possibly leading to considerable losses of chlorine.

It is extremely disadvantageous consequently to use a single reactor for the continuous side chain chlorination, for example as described in Pat. No. 15 100 of the German Democratic Republic. It has therefore been proposed in the past to use several reactors connected in cascade form (cf. for example U.S. Pat. No. 3,580,854). With reference to the above details it is understandable that the reaction takes place more rapidly in the first reactor of a cascade than in the last reactor, while the chlorine content is lower, and that a definite reactor volume may be utilized more economically if more reactors are present in a cascade. It is quite natural that the increase in the space-time yield is smaller when passing from 8 to 9 reactors than when passing from one to two reactors. As the technical expenditure, for example, for energy, radiation, measurement and control techniques increases with an increasing number of reactors, an optimum had to be found with regard to economy.

It was therefore necessary to develop a process overcoming the disadvantages of the processes hitherto known and enabling the obtaining of high qualtity products as well as an increase in the yield of the desired products, calculated on the quantity of chlorine charged. It was moreover necessary to develop a device for carrying out such a process and to indicate the required reaction conditions.

A process has now been found for the continuous preparation or mono- or di-(trichloromethyl)-benzenes being optionally substituted in the benzene ring by halogen atoms, preferably once or twice, from the corresponding mono- or dimethylbenzenes and chlorine in several steps with radiation by means of rays of high energy, which comprises reacting mono- or dimethylbenzene with chlorine in 4 to 14 steps, preferably 6 to 10 steps, at a temperature of from 20° to 130° C, preferably 40° to 110° C, by adding chlorine into the second step and the following steps, passing the resulting waste gas to the first step and reacting chlorine contained in the waste gas in the first step with fresh mono- or dimethylbenzene. In this process it is also possible to introduce the waste gas of increasing chlorine content of the final steps of the chlorination, for example the fifth and the following steps, to step 1 via step 2 or via steps 2 and 3.

Among radiations of high energy for the catalysis of the chlorination reaction ultraviolet light is used preferably.

The total of the waste gas leaving step 1 has a chlorine content of less than 1% by volume. This signifies that practically all chlorine used in the process is reacted in the intended manner, while high yields of the desired products of the invention are obtained calculated on chlorine charged. The process of the invention consequently signifies a surprising technical progress. It is moreover very economic, has low pollution effects and renders unnecessary the simultaneous use of inert gas.

The process of the invention may be carried out in various apparatuses, for example in reactors connected in cascade form and being provided with agitator vessels and submergible lamps for the individual stages.

BRIEF DESCRIPTION OF THE DRAWINGS

The invention will be illustrated by way of example in the accompanying drawings.

Figure 3:
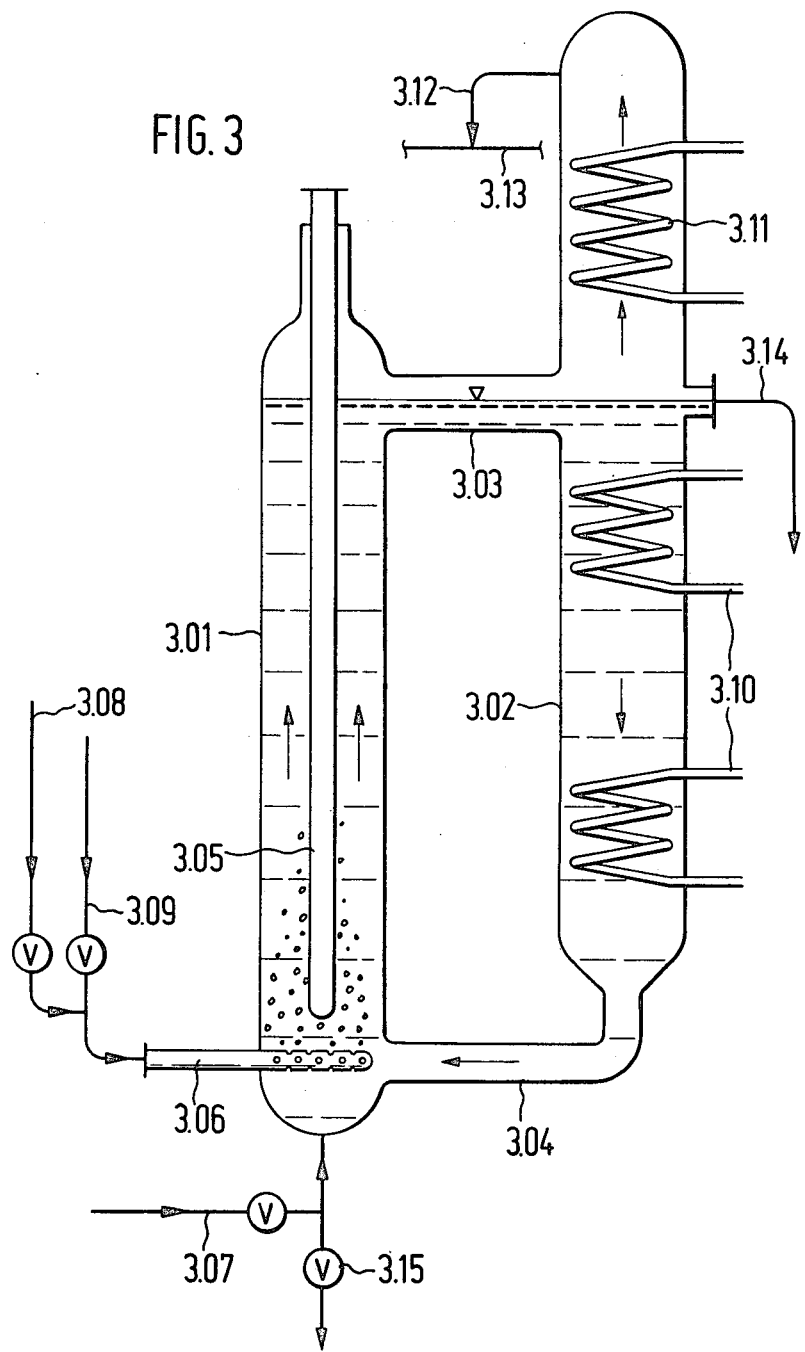
FIG. 3 represents a cross-section of the device for carrying out the process of the invention.

In a preferred form of the device for carrying out the aforesaid process a number of special circulation reactors, also named loop reactors, as represented in the FIG. 3, corresponding to the stages of the process are series-connected. According to this form a circulation reactor of the invention comprises the reactor parts 3.01 and 3.02, linked by the connecting pieces 3.03 and 3.04. The reactor part 3.01 is provided with a submersible ultraviolet light lamp 3.05 as well as with a gas introduction element 3.06. The addition of the mono- and dimethylbenzene compound to be chlorinated or its chlorination mixtures into the reactor part 3.01 is effected via inlet 3.07. The addition of chlorine gas or of the waste gas containing chlorine may be performed via inlets 3.08 or 3.09 in connection with the gas introduction element 3.06.

The reaction heat liberated in the course of the chlorination may be dissipated via the heat exchanger 3.10. The waste gas leaves the reactor via the gas condenser 3.11 and is introduced to a waste gas collecting conduit 3.13 via conduit 3.12. The overflow of the liquid chlorination mixture enters the reactor following each time or in the case of the last reactor of a cascade into a basin, via conduit 3.14. The reactor may be emptied via the valve 3.15.

The liquid circulation in the reactor according to the invention is substantially achieved by the gas added via the gas introduction element 3.06 in the form of ascending, finely divided chlorine gas bubbles or waste gas bubbles. In the upper part of the reactor the waste gas leaving the reactor through the gas condenser 3.11 and the liquid chlorination mixture are separated, the latter descending thereby into the part of the reactor 3.02 owing to cooling and thus intensifying the liquid circulation. It is moreover extremely advantageous that only layers of the chlorination mixture of relatively small thickness may form around the source of radiation due to the construction of the reactor. Thus a high catalytical activation effect results from the radiation, while a turbulent flow is simultaneously obtained.

Suitable construction materials for the reactor are preferably glass, but circulation reactors of enamel or nickel may likewise be used.

In order to avoid chlorinations in the nucleus there may only be used as engineering materials for the reactor compounds free from iron or compounds which do not liberate iron compounds, even in small quantities and which are moreover inert under the reaction conditions. Especially convenient are for example glass, enamel and nickel. Reactors lined with lead or plastic materials may also be used.

It has been noticed that the number of reactors required in the chlorination of mono- or dimethylbenzenes substituted in the benzene nucleus by halogen is smaller than that required in the chlorination of unsubstituted mono- or dimethylbenzenes. It has moreover become evident that the addition of chlorine into the individual reactors must be carried out carefully owing to the fact that the quantity of chlorine reacted generally is reduced in each reactor following the first one, besides the aforesaid characteristics of the chlorination reaction. The waste gas in the last reactor has consequently a higher content of chlorine, although the reactor is already charged with a corresponding lower quantity thereof. It has been noticed in this connection that the quantity of chlorine in the waste gas of the last reactor of the cascade should not exceed about 55% by volume, preferably it should be in the range of from 40 to 45% by volume. An addition of chlorine in the last reactor may be dispensed with, when the quantity of chlorine dissolved in the reaction product amounts to a multiple of the conversion attended there. This applies generally to cascades comprising 7 or more reactors. As the waste gas leaving the final reactors generally contains an increasing quantity of chlorine, it may be advantageously introduced firstly to reactor 2 or optionally to the reactors 2 and 3 of the cascade, where the portion of chlorine is reacted to a large extent together with the chlorine added there freshly. The waste gas of all reactors beginning with reactor 2, is finally introduced into the first reactor, which does not contain fresh chlorine. In the latter reactor the portion of chlorine of the waste gas is practically completely reacted with the mono- or dimethylbenzene compound used as starting compound so that the total of the waste gas of the process substantially consisting of hydrogen chloride contains less the 1% by volume of chlorine.

The pressure under which the chlorination reaction of the invention is performed is not critical. It is however preferably operated under atmospheric pressure. Lower of higher pressure are likewise possible, but do not bring about any advantages. The pressure should be advantageously chosen such that chlorine is in a gaseous state at the reaction temperature maintained and that the boiling point of the reaction liquid cannot be attained.

The temperature range for performing the chlorination reaction according to the invention is from 20° to 130° C, preferably from 40° to 110° C.

The following compounds may be used as starting products for the process according to the invention: toluene, chlorotoluenes, p-bromotoluene, m-fluorotoluene, 2,4-dichlorotoluene, xylenes, 5-fluoro-1,3-dimethylbenzene. Toluene, p-chlorotoluene, p-xylene, and m-xylene are preferably used, toluene and p-chlorotoluene particularly preferably.

As starting compounds there may also be used such mono- or dimethylbenzenes wherein the methyl groups are partially halogenated, for example benzylchloride.

The mono- or di-(trichloromethyl)-benzenes prepared according to the invention are obtained in a high yield and with a very good quality. Their content of secondary components containing dichloromethyl groups is at most 0.3% by weight. In a number of mono- or dimethylbenzenes further secondary products may be found in the final product in an amount of from about 0.1 to 3% by weight. The final product obtained in the chlorination of p-chlorotoluene, for example has a purity of 99.5% and when using as starting compound toluene the degree of purity of the final product is more than 97%. The high purity of the product of the invention permits using it as intermediate without any complicated purifying operations.

The mono- and di-(trichloromethyl)-benzenes are valuable intermediates for the preparation of pesticides, textile auxiliaries and dyestuffs.

The following examples illustrate the invention.

EXAMPLE 1

Figure 1:
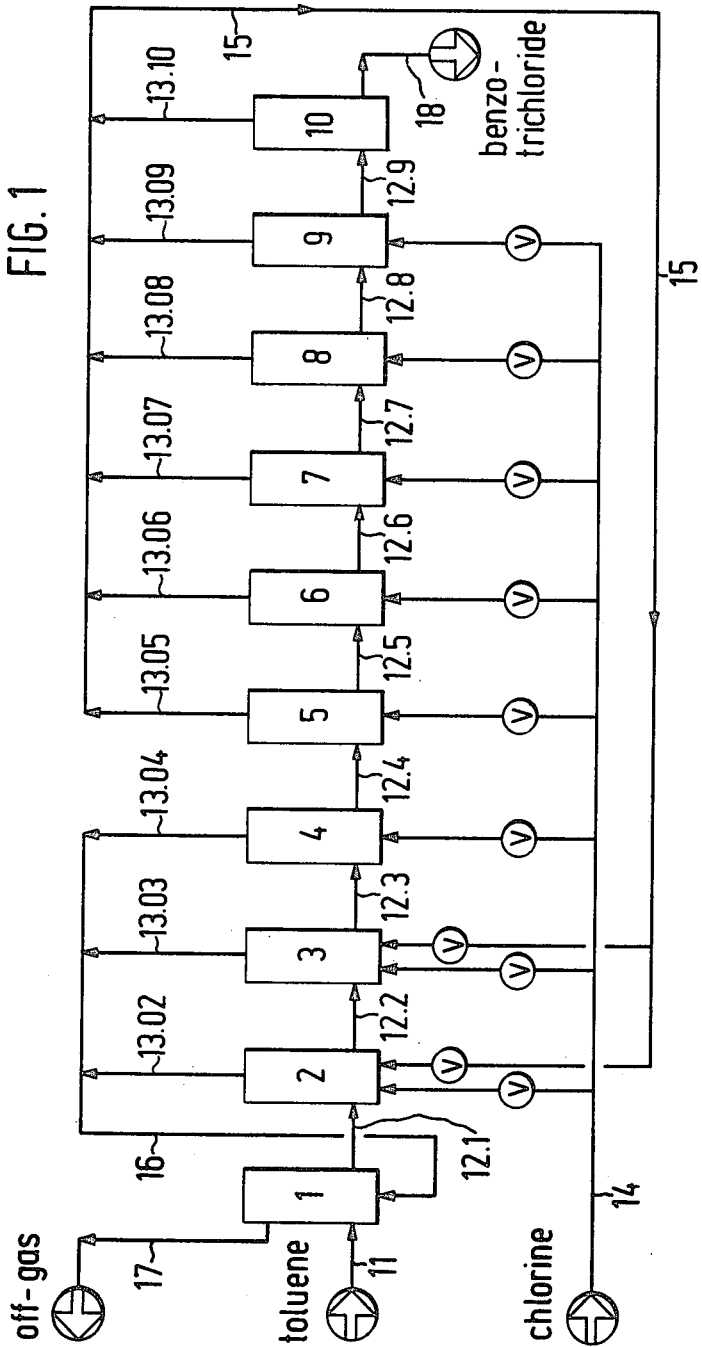
FIGS. 1 and 2 are flow schemes of the process of the invention.

In a reactor arrangement connected in cascade form as represented in the FIG. 1, made from glass, comprising 10 circulating reactors provided with mercury vapor lamps, according to FIG. 3 there were reacted per hour 3,150 mols of toluene and 9,321 mols of chlorine continuously to yield benzotrichloride. The temperature in the reactor 1 was in the range of from 50° to 70° C and in the reactors 2 to 10 from 85° to 95° C. The addition of chlorine was effected in reactors 2 to 9 via the inlet 14. Toluene was added to the reactor 1 via the inlet 11 and passed through the reactors 2 to 10 via the conduits 12.1 to 12.9 while forming benzotrichloride. 3,100 Mols per hour of benzotrichloride were obtained via conduit 18 in a crude state. The waste gas of the reactors 5 to 10 was passed to the reactors 2 and 3 via conduits 13.05 to 13.10 and the collecting conduit 15. The waste gas from the reactors 2 to 4 was passed to the reactor 1 via the conduits 13.02 to 13.04 and the collecting conduit 16. The waste gas leaving the reactor 1 via the conduit 17 comprised substantially hydrogen chloride and was practically free from chlorine gas. The crude benzotrichloride obtained continuously had a purity of about 98% by weight. It contained as secondary components 0.25% by weight of benzalchloride and 1.75% by weight of further chlorine-containing secondary products. Details concerning the course of the continuous chlorination reaction and the feeding of the reactors 1 to 10 may be seen in Table 2. The additions of the substances fed in the individual cascade stages in Table 2 are indicated as follows: the addition of toluene in mol/h, the addition of chlorine in mol of $Cl_2$/h, the addition of waste gas into the reactors 2 and 3 in mol of HCl/h. By incorporation of chlorine in % there is to be understood the portion in percent of chlorine absorbed by the charged toluene with regard to the stoichiometrical reaction yielding benzotrichloride, measured each time at the moment when the reaction mixtures left the corresponding reactor.

6,669 mols of chlorine continuously to yield p-chlorobenzotrichloride. The temperatures in the reactor 1a were in the range of from 70° to 80° C and in the reactors 2a to 6a of from 90° to 100° C. The addition of chlorine into the reactors 2a to 6a was effected via the inlet 22. P-chlorotoluene was lead to the reactor 1a via conduit 19 and passed through the reactors 2a to 6a via the connecting conduits 20.1 to 20.5 while forming p-chlorobenzotrichloride. 2,225 Mols of p-chlorobenzotrichloride per hour were obtained in a crude state via the connecting conduit 21. The waste gas from the reactors 2a to 6a was passed to the reactor 1a via the conduits 23.2 to 23.6 and the connecting conduit 24. The waste gas leaving the reactor 1a via the conduit 25 substantially consisted of hydrogen chloride and was practically free from chlorine gas. The p-chlorobenzotrichloride obtained continuously in a crude state had a degree of purity of more than 99.5% by weight. It contained as secondary components 0.2% by weight of p-chlorobenzalchloride and 0.25% by weight of further chlorine-containing secondary products. Details concerning the course of the continuous chlorination reaction as well as the feeding of the reactors 1a to 6a may be found in Table 3.

In Table 3 the addition of chlorotoluene in the individual cascade stages is indicated in mol/h, the addition of chlorine in mol of $Cl_2$/h, the incorporation of chlorine (defined in Example 1) in % as well as the yield of crude p-chlorobenzotrichloride in mol/h.

TABLE 3

Continuous chlorination of p-chlorobenzochloride according to Example 2

| cascade stage (reactor No.) | 1a | 2a | 3a | 4a | 5a | 6a | sum (1a to 6a) |
|---|---|---|---|---|---|---|---|
| addition of p-chlorotoluene (mol/h) | 2230 | | | | | | 2230 |
| addition of chlorine (mol of $Cl_2$/h) | | 2548 | 2601 | 1182 | 261 | 77 | 6669 |
| incorporation of chlorine (%) | 18.5 | 54.8 | 85.4 | 97.3 | 99.5 | 99.9 | 99.9 |
| yield of crude chlorobenzotrichloride (mol/h) | | | | | | 2225 | 2225 |

TABLE 2

Continuous chlorination of toluene yielding benzotrichloride according to Example 1

| cascade stage (reactor No.) | 1 | 2 | 3 | 4 | 5 | 6 | 7 | 8 | 9 | 10 | sum (1 to 10) |
|---|---|---|---|---|---|---|---|---|---|---|---|
| addition of toluene (mol/h) | 3150 | | | | | | | | | | 3150 |
| addition of chlorine (mol of $Cl_2$/h) | | 2398 | 2384 | 2360 | 1144 | 584 | 269 | 124 | 58 | | 9321 |
| addition of waste gas (mol/h) | | | | | | | | | | | |
| HCl | | 736 | 957 | | | | | | | | |
| $Cl_2$ | | 211 | 275 | | | | | | | | |
| chlorine conversion (mol/h) | 618 | 2573 | 2428 | 1950 | 930 | 465 | 205 | 84 | 29 | 9 | 9291 |
| incorporation of chlorine (%) | 6.7 | 34.3 | 60.4 | 81.4 | 91.4 | 96.4 | 98.6 | 99.5 | 99.8 | 99.9 | 99.9 |
| crude benzotrichloride (yield in mol/h) | | | | | | | | | | 3100 | 3100 |

EXAMPLE 2

Figure 2:
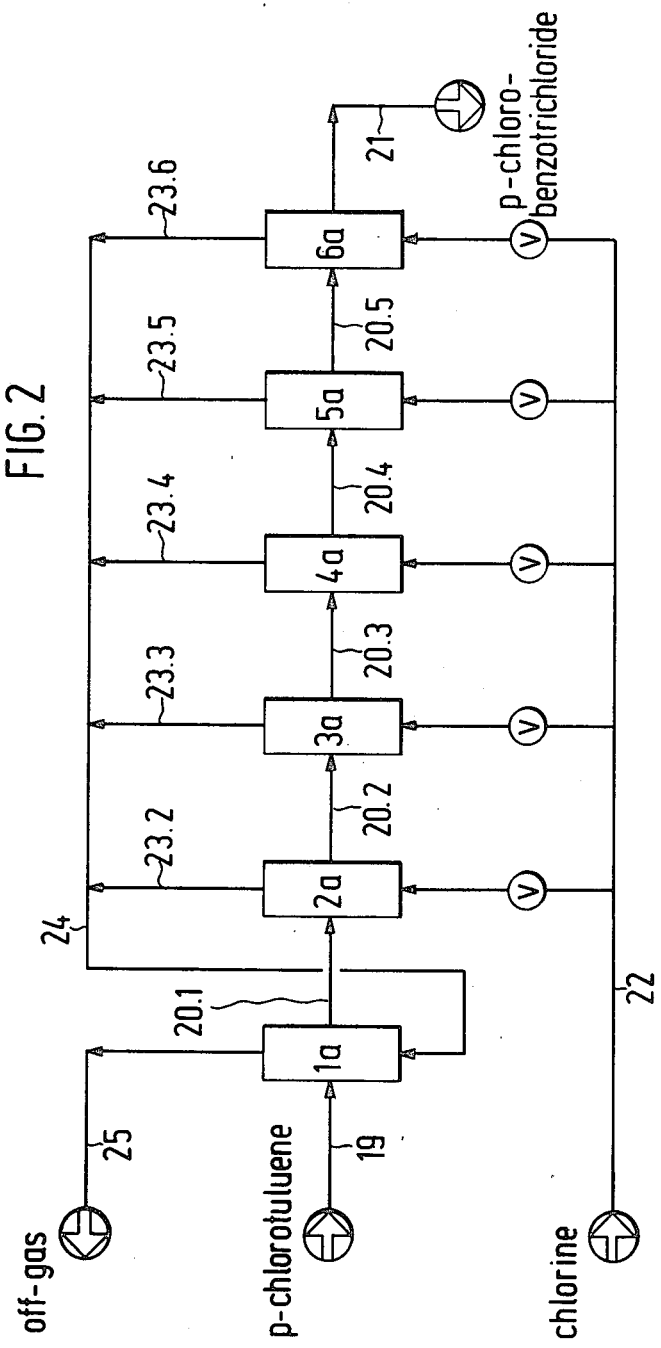

In the reactor arrangement made from glass connected in cascade form as represented in the FIG. 2, comprising six circulation reactors provided with mercury vapor lamps according to the FIG. 3, there were reacted per hour 2,230 mols of p-chlorotoluene and

We claim:

1. In a process for the continuous preparation of a mono- or di-(trichloromethyl)-benzene, or a mono- or di-(trichloromethyl)-benzene halo-substituted in the benzene ring, from the corresponding unsubstituted or halo-substituted mono- or dimethylbenzene, or said unsubstituted or halo-substituted mono- or dimethylbenzene which is mono- or dihalo-substituted in one or both methyl groups, and chlorine in several steps by irradiating with actinic light, the improvement which comprises reacting said unsubstituted or halo-substituted mono- or dimethylbenzene, or said unsubstituted or halo-substituted mono- or dimethylbenzene which is mono- or dihalo-substituted in one or both methyl groups, in four to 14 steps with chlorine, by introducing chlorine to the second step and the following steps, or to the second and following steps excluding the last step when the quantity of chlorine dissolved in the reaction product amounts to a multiple of the expected conversion, introducing the resulting waste gas to step 1 and reacting the chlorine contained in the waste gas there with fresh said corresponding unsubstituted or halo-substituted mono- or dimethyl benzene, or said unsubstituted or halo-substituted mono- or dimethylbenzene which is mono- or dihalo-substituted in one or both methyl groups.

2. The process as defined in claim 1, which comprises carrying out the reaction in six to 10 steps.

3. The process as defined in claim 1, which comprises carrying out the reaction at a temperature of from 40° to 110° C.

4. The process as defined in claim 1, which comprises irradiating with ultraviolet light.

5. The process as defined in claim 1, wherein chlorine is introduced to the second and following steps.

6. The process as defined in claim 1, which comprises introducing the waste gas of the final chlorination steps to step 2 or steps 2 and 3, and the waste gas of step 2 or steps 2 and 3, respectively, to step 1.

7. The process as defined in claim 1, which comprises carrying out the reaction in a reactor arrangement in cascade form, the number of the steps corresponding to the number of the reactors.

8. The process as defined in claim 7, wherein the reactors are circulation reactors.

9. The process as defined in claim 8, wherein the circulation reactors are glass.